(12) United States Patent
Klimovitch (10) Patent No.: US 9,566,107 B2
(45) Date of Patent: Feb. 14, 2017

(54) METHOD AND APPARATUS FOR RADIOFREQUENCY ABLATION WITH INCREASED DEPTH AND/OR DECREASED VOLUME OF ABLATED TISSUE

(75) Inventor: Gleb V. Klimovitch, Santa Clara, CA (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 773 days.

(21) Appl. No.: 12/428,173

(22) Filed: Apr. 22, 2009

(65) Prior Publication Data

US 2010/0274238 A1  Oct. 28, 2010

(51) Int. Cl.
*A61B 18/00* (2006.01)
*A61B 18/14* (2006.01)

(52) U.S. Cl.
CPC ........ *A61B 18/1442* (2013.01); *A61B 18/1447* (2013.01); *A61B 2018/00577* (2013.01); *A61B 2018/1467* (2013.01)

(58) Field of Classification Search
CPC .............. A61B 2018/00577; A61B 18/1445; A61B 2018/00589; A61B 2018/0063; A61B 2018/00607; A61B 18/1442; A61B 18/1447; A61B 2018/1467
USPC ........ 606/32, 33, 34, 35, 37, 38, 39, 40, 41, 42,606/45, 48, 49, 50, 51, 52
See application file for complete search history.

(56) References Cited

U.S. PATENT DOCUMENTS

| 5,383,917 | A | * | 1/1995 | Desai et al. | 607/102 |
|---|---|---|---|---|---|
| 5,688,270 | A | * | 11/1997 | Yates et al. | 606/51 |
| 5,693,051 | A | * | 12/1997 | Schulze et al. | 606/51 |
| 5,755,717 | A | * | 5/1998 | Yates et al. | 606/51 |
| 5,810,811 | A | * | 9/1998 | Yates et al. | 606/50 |
| 5,921,984 | A | * | 7/1999 | Sutcu et al. | 606/46 |
| 6,059,778 | A | | 5/2000 | Sherman | |
| 6,086,586 | A | * | 7/2000 | Hooven | 606/50 |
| 6,102,909 | A | * | 8/2000 | Chen et al. | 606/45 |
| 6,162,220 | A | * | 12/2000 | Nezhat | 606/48 |
| 6,821,273 | B2 | * | 11/2004 | Mollenauer | 606/28 |
| 6,837,887 | B2 | * | 1/2005 | Woloszko et al. | 606/41 |
| 6,984,233 | B2 | | 1/2006 | Hooven | |
| 7,241,292 | B2 | | 7/2007 | Hooven | |

(Continued)

FOREIGN PATENT DOCUMENTS

WO  9956644  11/1999
WO  9956648  11/1999

*Primary Examiner* — Kevin C Sirmons
*Assistant Examiner* — William Carpenter
(74) *Attorney, Agent, or Firm* — Dykema Gossett PLLC (57) ABSTRACT

A method of ablating a tissue site includes at least two stages. A first stage involves conducting bipolar ablation between a first pair of electrodes situated in an opposing arrangement on opposing sides of the tissue site to form a pair of opposing first stage ablation regions extending from respective sides of the tissue towards the center. A second stage involves conducting bipolar ablation between a second pair of electrodes situated in a diametrical arrangement with respect to the first stage ablation regions, which forms a second stage ablation region intermediate the pair of first stage ablation regions. The second stage completes the ablation through the entire depth of the tissue site. Since the overall process can accommodate incomplete ablation during the first stage, lower power, reduced ablation times or both may be used during the first stage, avoiding overheating and with a decrease in ablated tissue volume.

22 Claims, 7 Drawing Sheets (56) References Cited

U.S. PATENT DOCUMENTS

| | | |
|---|---|---|
| 7,263,397 B2 | 8/2007 | Hauck et al. |
| 7,877,853 B2 * | 2/2011 | Unger et al. ................. 29/592.1 |
| 7,931,649 B2 * | 4/2011 | Couture et al. ................. 606/51 |
| 7,959,626 B2 * | 6/2011 | Hong et al. ...................... 606/34 |
| 2002/0111624 A1 * | 8/2002 | Witt et al. ....................... 606/51 |
| 2005/0004569 A1 * | 1/2005 | Witt et al. ....................... 606/51 |
| 2005/0043727 A1 * | 2/2005 | Swanson et al. ............... 606/41 |
| 2006/0217699 A1 * | 9/2006 | Wang et al. .................... 606/32 |
| 2008/0015562 A1 | 1/2008 | Hong et al. |
| 2010/0022999 A1 * | 1/2010 | Gollnick et al. ................ 606/33 |

* cited by examiner

METHOD AND APPARATUS FOR RADIOFREQUENCY ABLATION WITH INCREASED DEPTH AND/OR DECREASED VOLUME OF ABLATED TISSUE

BACKGROUND OF THE INVENTION a. Field of the Invention

The present disclosure relates generally to ablation systems, and more particularly, to a method and apparatus for radiofrequency ablation with increased depth and/or decreased volume of ablated tissue.

b. Background Art

It is known to deliver radiofrequency (RF) energy to a desired target area through an electrode assembly to ablate tissue at the target site. RF ablation may generate significant heat, which if not controlled can result, generally, in undesired or excessive tissue damage. It is particularly difficult to achieve successful RF ablation of live, relatively thick biological tissue, for a number of reasons. The cross-sectional profile (i.e., depth) of ablation is often too shallow, in part because most of the Ohmic heat is generated near the RF electrodes, i.e., at the surface of the tissue. Furthermore, the rate at which heat diffuses deep into the tissue layer(s) is extremely slow, and may be counteracted by the cooling effects due to blood perfusion, for example, during epicardial ablation. As the tissue surrounding the electrodes is being ablated, its Ohmic resistivity increases. This increase in resistivity further exacerbates the problem of non-uniform heating, because at a given current density, the heating intensity experienced by the tissue is proportional to its then-existing Ohmic resistivity.

Moreover, the goals of thick layer RF cardiac ablation are often at odds. It is often necessary to ablate all the way through the thickness of the tissue, while at the same time avoiding tissue overheating and minimizing the volume of ablated tissue. However, the thicker the tissue layer, the less possible it is to achieve adequate ablation through its thickness without overheating the tissue near the RF electrodes (i.e., damaging the tissue in an unacceptable way) and without ablating an undesirable excess volume of tissue.

There are a number of two-electrode or multi-electrode RF ablating devices known in the art, for example as seen by reference to U.S. Pat. No. 7,241,292 entitled CARDIAC ABLATION DEVICE WITH MOVABLE HINGE issued to Hooven. Hooven discloses a transmural RF ablation device. However, Hooven does not address the problems of inadequate ablation depth or excessive ablated tissue volume described above, particularly for a relatively thick biological tissue layer.

There is therefore a need to minimize or eliminate one or more of the problems set forth above.

BRIEF SUMMARY OF THE INVENTION

One advantage of the methods and apparatus described, depicted and claimed herein relates to increased depth of RF ablation lesions while at the same time reducing the overall volume of ablated tissue as compared to known approaches.

This disclosure is directed to methods of ablating tissue site between diverse electrode pairs and the methods include at least two discrete ablation procedure stages. During a first stage, an embodiment of the inventive method involves conducting radiofrequency (RF) energy (e.g., bipolar or unipolar RF energy) ablation between a first pair of electrodes situated in an opposing arrangement on opposing sides of the tissue site. The first stage ablation forms a pair of opposing first stage ablation regions extending from respective sides of the tissue towards the center of the site. However, the first stage may not completely ablate the site through its depth. During a second stage in one form of the invention, the methods involve conducting bipolar ablation but between a second pair of electrodes situated in a diametrical arrangement with respect to the first stage ablation regions. The second stage ablation forms a second stage ablation region intermediate the first stage ablation regions, effectively bridging the pair of first stage ablation regions. To the extent an un-ablated channel, region or gap exists between the pair of opposing ablation regions after the first stage, the second stage completes the ablation through the entire depth of the tissue site. Since the invention can accommodate incomplete ablation or non-transmural ablation lesions (i.e., a lesion due to ablation that does not penetrate the entire depth of the tissue site) during the first stage, lower power, reduced ablation times or both may be used during such first stage, with a resultant decrease in ablated tissue volume. The second stage completes the ablation process throughout the tissue depth, providing increased depth. As note, unipolar or bipolar electrical configurations can be used, or combinations of each type of energy delivery.

A system for RF ablation according to the invention is also presented. In such a system a pair of opposing substantially resilient elongate members couple electrodes for RF energy delivery therebetween. The elongate members can comprise clamping members actuated via a pivot such a scissor-like unit or a pair of members slideably coupled so that one is fixed and the other moveable toward the fixed member. Suitable elongate conductors, switches couple the electrodes to an RF generator. In one form the members are designed and fabricated of biocompatible material and of dimension providing ease of pericardial access via, for example, a sub-xiophoid incision to access one or more pulmonary veins of a subject. In another form, the elongate members comprise at least two pairs of opposing members so that both pairs can engage a target tissue site in a compressive state and at least one can be relaxed in a non-compressive state thereby not engaging the target tissue site. In another form an insulative sheath can be advanced over one or more of the electrodes to selectively insulate same from the target tissue site during subsequent ablation procedures. The electrodes can be coupled to only an RF generator or one or more electrodes can also couple to a cardiac pacing circuit and/or a cardiac sensing circuit or impedance measuring circuit according to various forms of the invention. The pacing and/or sensing circuitry can be used to confirm transmurality of a particular lesion set (e.g., a continuous transmural lesion around a plurality of pulmonary veins) whether or not the set was produced by a system according to the foregoing or in part by another apparatus. That is, pacing or sensing "above" the lesion set (above natural sinus rhythm) should not conduct or capture the myocardium thus indicating continuity of the lesion set. Likewise, sensing above the lesion set should not detect cardiac activity (or at least not at typical amplitude(s)).

These and other benefits, features, and capabilities are provided according to the structures, systems, and methods depicted, described and claimed herein.

DETAILED DESCRIPTION OF THE INVENTION

Figure 1:
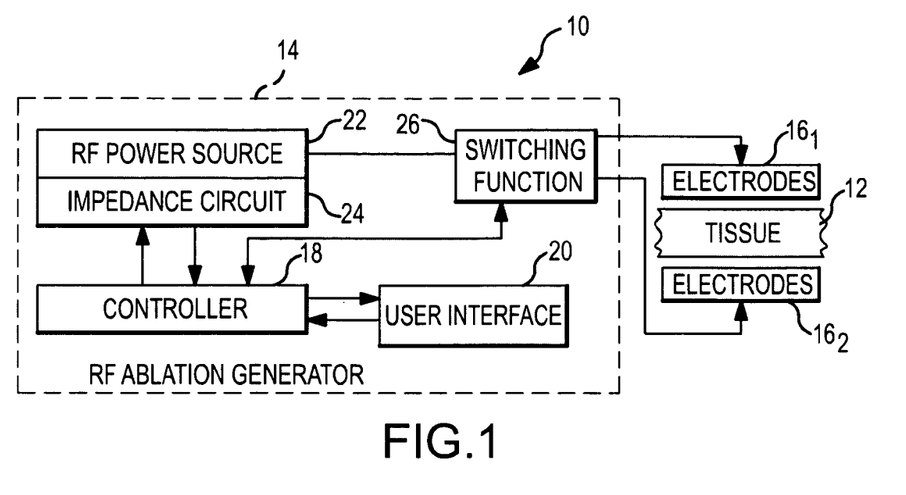
FIG. 1 is a block and diagrammatic view of an apparatus for RF ablation of a tissue layer, in an embodiment.

Referring now to the drawings wherein like reference numerals are used to identify identical components in the various views, FIG. 1 is a simplified block and diagrammatic view of a system 10 for conducting RF ablation of a live, biological tissue site 12. The system 10 is configured to increase the depth of lesions created through RF ablation as well as reduce the volume of ablated tissue for a given tissue thickness. The method divides the ablation process into two main stages, which, without loss of generality, will be described in connection with a number of bipolar ablation embodiments. Although there are many possible uses of the present invention, one in particular may involve epicardial ablation, such as, for example, as therapy in connection with the treatment of atrial fibrillation. In this regard, the tissue site 12 may comprise either a single layer of tissue (e.g., tissue wall), or may alternately comprise a pinched or clamped pair of tissue layers such as described and illustrated in U.S. Pat. No. 7,231,292 to Hooven (noted in the Background), herein incorporated by reference in its entirety. Of course, other applications and purposes are possible, as understood in the art.

With continued reference to FIG. 1, the system 10 may include an energy source, such as an RF ablation generator 14. The RF ablation generator 14 may serve to facilitate the operation of an ablation procedure and may involve monitoring any number of chosen variables (e.g., temperature of the ablation electrode, ablation energy, duration) and providing the requisite energy source to electrodes, shown in block form as electrode blocks $16_1$ and $16_2$.

The ablation generator 14 may include a main controller 18, a user interface 20, an RF power source 22 and optionally an impedance detection circuit 24. The main controller 18 may be configured to control the operation of the RF power source 22 in accordance with various inputs (e.g., power setting, ablation duration (time), etc.) received from a user thereof through the user interface 20. The controller 18 may be further configured interact with the impedance detection circuit 24 to obtain data indicative of an impedance value measured through or using one or more of the electrodes within electrode blocks $16_1$, $16_2$ and to communicate and/or control the user interface 20 to display or otherwise communicate the measured impedance to a user. The RF power source 22 may typically produce RF signals in the frequency range of between about 50 kHz and 500 kHz. The controller 18 may be still further configured to control a switching function block 26 to make the connections between the RF power source 22 and the plurality of electrodes contained in the electrode blocks $16_1$, $16_2$, in a manner that will become more apparent from the detailed description below. The controller 18, user interface 20, RF power source 22, impedance detection circuit 24 and switching function block 26 may each comprise conventional components known to those of ordinary skill in the art, except as may be otherwise noted herein. For example, the RF ablation generator 14 may comprise conventional apparatus, such as a commercially available unit sold under the model number IBI-1500T RF Cardiac Ablation Generator, available from Irvine Biomedical, Inc. Of course, the RF ablation generator 14 can also comprise other known energy sources. The art is replete with RF ablation generator configurations, designs, implementations and the like, and will therefore not be described in any further detail.

Additional components (not shown) may also be integrated into the system 10, such as visualization, mapping and navigation components known in the art, including among others, for example, an EnSite™ Electro Anatomical Mapping System commercially available from St. Jude Medical, Inc., and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present invention, and hereby incorporated by reference in its entirety. Additionally, an electrophysiological (EP) monitor or display such as an electrogram signal display, or other systems conventional in the art may also be integrated into the system 10. It should be understood that embodiments consistent with the present invention may, and typically will, include other features not shown or described herein in FIG. 1 for the sake of brevity and clarity.

Figure 2:
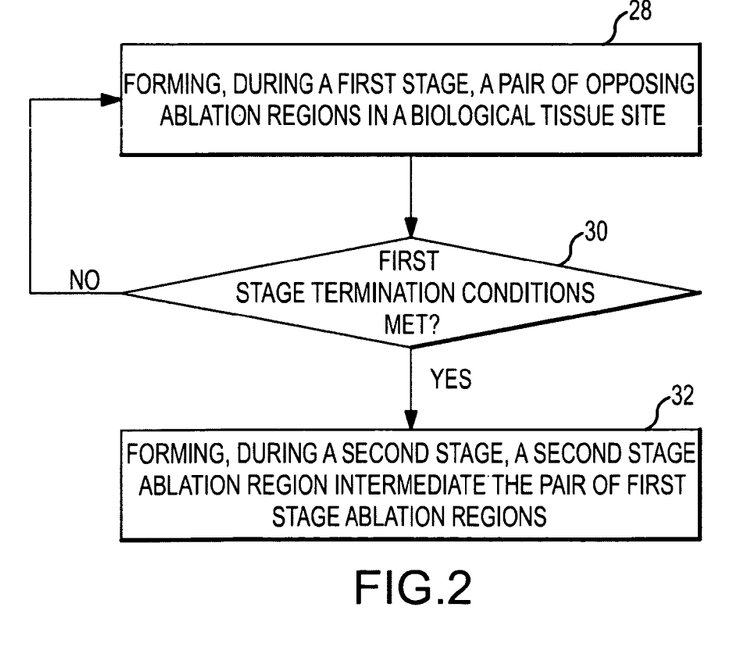
FIG. 2 is a flow chart diagram of a method of ablating the tissue site as shown in FIG. 1.

FIG. 2 is a flow chart showing steps of a method for two-stage RF ablation according to an embodiment of the invention. The method begins in step 28.

In step 28, the method involves conducting, during a first stage, bipolar ablation between a first pair of electrodes situated in an opposing arrangement on opposing sides of the tissue site so as to form a pair of opposing first stage ablation regions. This step may or may not achieve complete transmural ablation (i.e., complete through the depth of the tissue site), and accordingly may leave a channel of un-ablated tissue between the first stage ablation regions. Since the two stage process can accommodate ablation that does not, during the first stage alone, achieve ablation through the complete depth of the tissue, the method contemplates that reduced power levels, reduced ablation durations (e.g., time) or other variations may be used, which has the desirable result of avoiding overheating and yielding a reduced volume of ablated tissue. The method proceeds to step 30.

In step 30, the method involves determining whether first stage termination conditions have been met. This step may be expressed in a number of different embodiments. In one embodiment, the user (e.g., practitioner) may set an initial power level (e.g., constant power level in watts) and duration, based on, for example, experience, patient/tissue site assessment and/or other factors known in the art. Accordingly, when the manually-set duration expires, the first stage ablation is complete. Alternatively, the termination conditions may involve assessment of the impedance between different pairs of electrodes, for example, when an impedance value is determined to saturate (i.e., increase to a certain level or by a certain amount or by a certain factor and then substantially level off). This impedance assessment may be made manually (i.e., by the user), or may be automated, in which case the main controller 18 is configured to monitor the impedance, as determined by the impedance detection circuit 24, and when the impedance saturation condition is detected, generating a control signal to the RF power source to automatically discontinue power (i.e., or otherwise discontinue application of power, such as by disconnecting the power source via opening of the switching devices in the switching function block 26, or in other ways known in the art). This impedance assessment feature will be described in greater detail below with respect to specific electrodes in specific embodiments. In any event, if the termination conditions have not been met ("NO"), then the method branches back to step 28, where the first stage ablation continues. However, if the first stage termination conditions are met ("YES"), then the method proceeds to step 32.

In step 32, the method involves further bipolar ablation, during a second stage, but now between a second pair of electrodes situated in a diametrical arrangement with respect to the first stage ablation regions (i.e., not the opposing arrangement described above). Because of the increased impedance exhibited by the first stage ablation regions, the tissue that may remain unablated after the first stage (i.e., the region between the first stage ablation regions) constitutes the proverbial "path of least resistance" for the ablation energy to be delivered and focused into during this second stage, given the diametrical arrangement of electrodes. The second stage is thus operative to form a second stage ablation region intermediate the opposing first stage ablation regions. The second stage ablation completes the ablation process, ensuring that the tissue site is ablated completely through its depth, without undesired, excessive volume of tissue being ablated.

Figure 3:
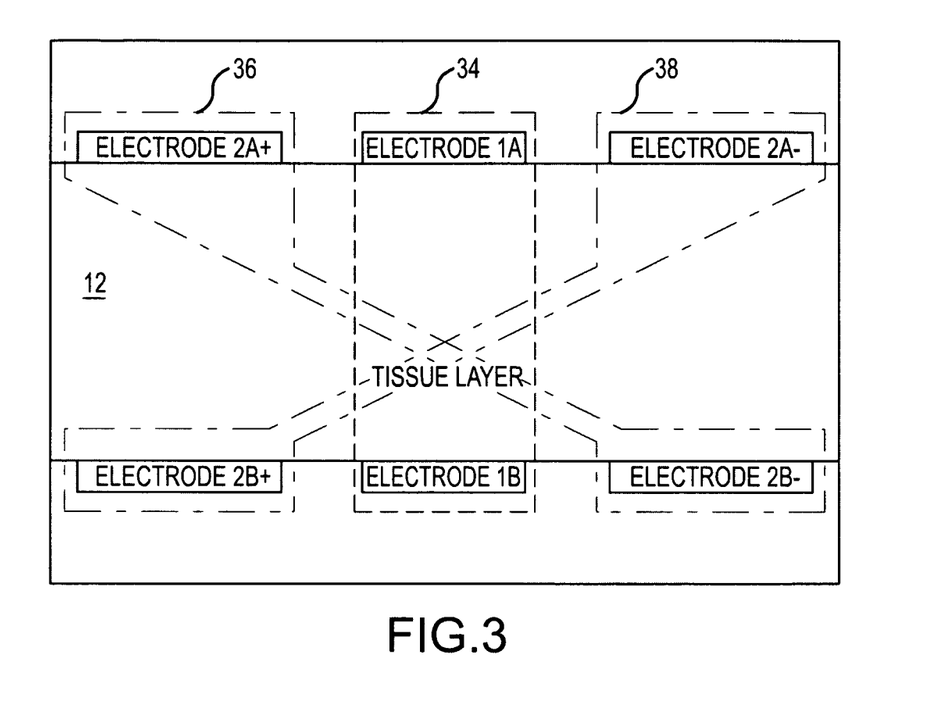
FIG. 3 is a cross-sectional view of a tissue site shown, in a first embodiment, in an initial un-ablated condition.

FIG. 3 is a cross-sectional view of a biological tissue site 12 showing an RF ablation electrode configuration in a first embodiment. As described above, the ablation process is conceptually divided into two stages, and without loss of generality, such process will be described for specific embodiments involving bipolar ablation under the following conditions: (1) the tissue-electrode interface is substantially flat; (2) the electrode width is small relative to its length (e.g., length≥width; preferably, length≥2*width, more preferably, length≥3*width); (3) the heating intensity produced by the electrode extends generally in a direction perpendicular to the electrode (when viewing the cross-sectional profile, e.g., as in FIG. 3), and moreover that the cross-sections shown in the various Figures are removed by at least several electrode-widths from the electrodes tips/forward edges; and (4) the RF electrodes that are not powered during a given ablation stage may be physically removed from tissue electrical contact or alternatively electrically isolated from the tissue, even though such electrodes may continue to be shown positioned on the tissue. With this understanding, a number of embodiments will now be described.

With continued reference to FIG. 3, the upper and lower electrode blocks $16_1$ and $16_2$ (e.g., as shown in FIG. 1 in block form) may be embodied as a first pair of electrodes 34 (i.e., electrodes designated 1A and 1B), a second pair of electrodes 36 (i.e., electrodes designated 2A+ and 2B−) and a third pair of electrodes 38 (i.e., electrodes designated 2A− and 2B+). The first pair of electrodes 34 are situated in an opposing arrangement on opposing sides of the tissue site 12, while the second and third pairs of electrodes 36, 38 are situated in first and second diametrical arrangements, respectively, i.e., as taken with respect to the first pair of electrodes 34 or the ablation regions they create. During the first stage, only the first pair of electrodes 34 (i.e., electrodes 1A and 1B) are powered in counter-phase by the RF ablation generator 14 for conducting bipolar ablation.

Figure 4:
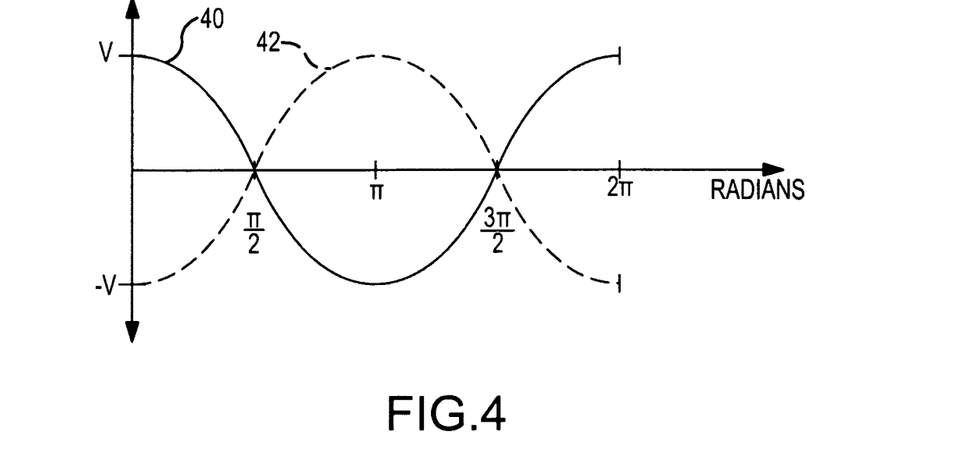
FIG. 4 is a timing diagram of voltage waveforms produced in counter-phase.

FIG. 4 shows one example of how two power signals 40, 42 may be produced in counter-phase. As illustrated, signals 40, 42 may be sinusoids, and further, may be offset in phase by 180 degrees ($\pi$ radians). It should be appreciated that through this counter-phase configuration, electrical current will alternately flow in both directions (i.e., from electrode 1A→1B, and alternately 1B→1A). It should be further understood that this configuration is exemplary only, and one of ordinary skill in the art will recognize a wide variety of alternatives to accomplish bipolar ablation between a pair of electrodes 34. The ablation generator 14, including the RF power source 22, is configured to produce RF power signals in accordance with the particular phasing approach chosen (e.g., here, a counter-phase approach). It should be further understood that still other variations are possible. For example, some unipolar component may be employed during the first stage of ablation.

For such unipolar component embodiments, the electrode configuration described herein would further include an indifferent or reference electrode, disposed either within the body or affixed to the body surface of the subject (i.e., skin patch electrode). The activation for the unipolar component (first stage) may involve, in one embodiment, sequential activation of the electrodes 1A and 1B of the electrode pair 34 (i.e., each electrode being vectored to the indifferent/reference electrode). Thus, while one electrode (e.g., electrode 1A) is activated, the opposing, non-activated electrode (e.g., electrode 1B) is electrically isolated from the tissue site, such as, for example, by removing the non-activated electrode from contact with the tissue site (i.e. spaced from the tissue—myocardium) or otherwise selectively electrically insulating the electrode from the tissue. In another unipolar component embodiment, both electrodes are electrically driven at the same time; however, not in counter-phase but rather with a phase offset greater than 0 degrees and less than 180 degrees (again, a reference/indifferent electrode is used). It bears emphasizing that to the extent unipolar ablation components are used, it would be used during the first stage ablation. The second stage ablation would continue to involve bipolar ablation.

Figure 5:
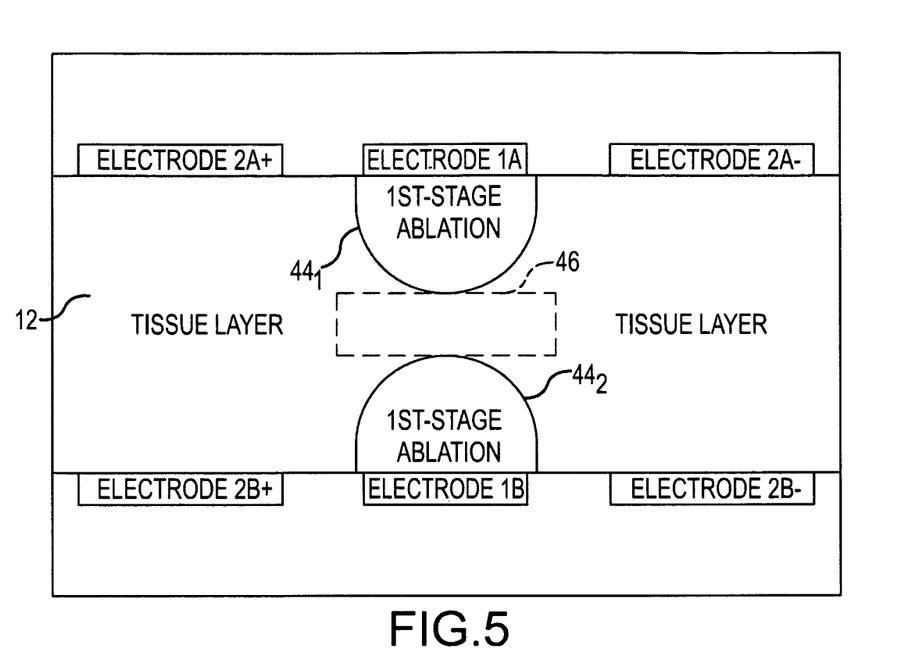
FIGS. 5-6 are cross-sectional views of the tissue site of FIG. 4, shown in the first and second stages of ablation, respectively.

FIG. 5 is a cross-sectional view (profile) of the tissue site 12 at the end of the first stage of ablation. Conducting bipolar ablation during the first stage forms a pair of opposing first stage ablation regions $44_1$, $44_2$ in the tissue at tissue site 12. At the end of the first stage, for a relatively thick tissue site 12, it is possible that the ablation did not progress all the way through the whole tissue depth, leaving an unablated region 46 in between the first stage ablation regions $44_1$, $44_2$. Further application of ablation power to the first pair of electrodes 34 (i.e., individual electrodes 1A and 1B) can result in overheating of the already-ablated tissue near these electrodes, since the impedance of the ablated tissue is often significantly higher than the impedance of the non-ablated tissue (i.e., at least within a predetermined, relatively short time after ablation, while such tissue is at an elevated temperature).

Figure 6:
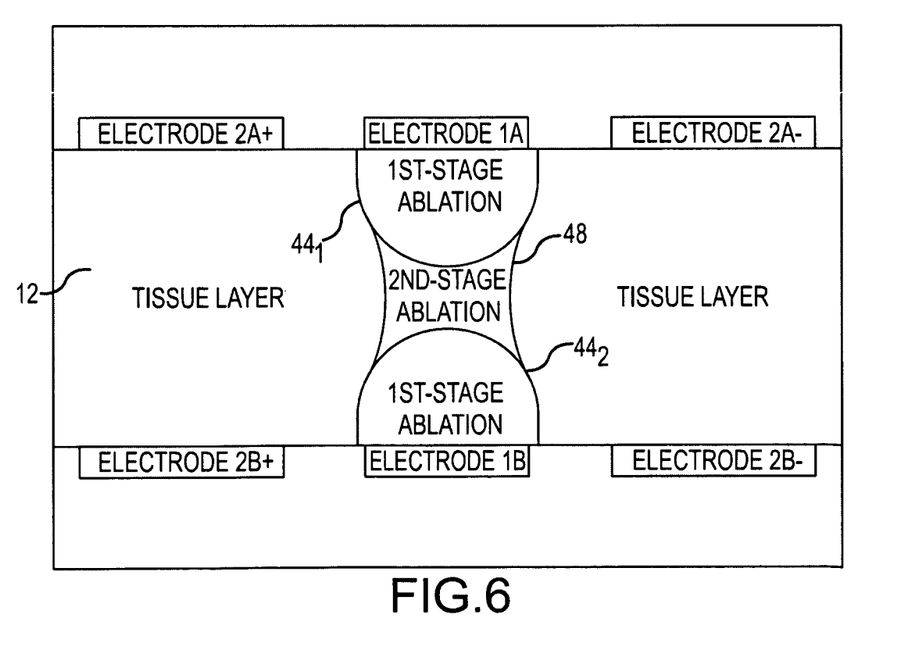

FIG. 6 is a cross-sectional (profile) view of the tissue site 12 during/after the second stage of ablation. To address the overheating and potentially undesirable increased volume of ablated tissue, the first stage is discontinued (e.g., the electrodes 1A/1B are de-energized and/or removed), and during the subsequent second stage, bipolar ablation is conducted using the second and third pairs of electrodes 36, 38. In the illustrated embodiment, bipolar ablation is conducted between electrodes 2A+ and 2B+(i.e., energized in a positive phase such as per signal 40 in FIG. 4) and electrodes 2A− and 2B− (i.e., energized in a negative phase such as per signal 42 in FIG. 4). The increase in the impedance of the first stage ablation regions $44_1$, $44_2$ near electrodes 1A/1B facilitates the ablation during the second stage, since this characteristic helps concentrate the RF current in and through the narrow, unablated channel (region 46 in FIG. 5) between the first stage ablation regions $44_1$, $44_2$. As a result, the tissue in and around the region 46 (FIG. 5) is ablated during the second stage, forming a second stage ablation region 48, without affecting significant tissue volumes in undesired regions.

In the embodiment of FIGS. 3 and 5-6, unnecessary ablation near the electrodes 2A+/2A− and 2B+/2B− is suppressed through a number of approaches: (1) by configuring the electrodes 2A+/2A− and 2B+/2B− so that they are wider than the electrodes 1A/1B; (2) by arranging the electrodes 2A+/2A− and 2B+/2B− so that they are laterally offset from the first stage ablation regions $44_1$, $44_2$ by at least a predetermined distance; and (3) by replacing each of the electrodes 2A+/2A− and 2B+/2B− with properly driven multiple electrodes.

In addition, to better concentrate RF current between the first stage ablation regions $44_1$, $44_2$, in one variation, the first pair of electrodes 34 (1A/1B) may be electrically isolated from the tissue site 12 so that these electrodes (1A/1B) will not partially shunt current via the first stage ablation regions $44_1$, $44_2$. Electrical isolation may be accomplished by physically removing the first pair electrodes 34 from electrical contact with the tissue site 12 or alternatively interposing a relatively high impedance material, such as an insulative sheath movable between a first conductive position and a second insulating position, between the first electrode pair 34 (1A/1B) and the RF power source 22 of the ablation generator 14.

Figure 7:
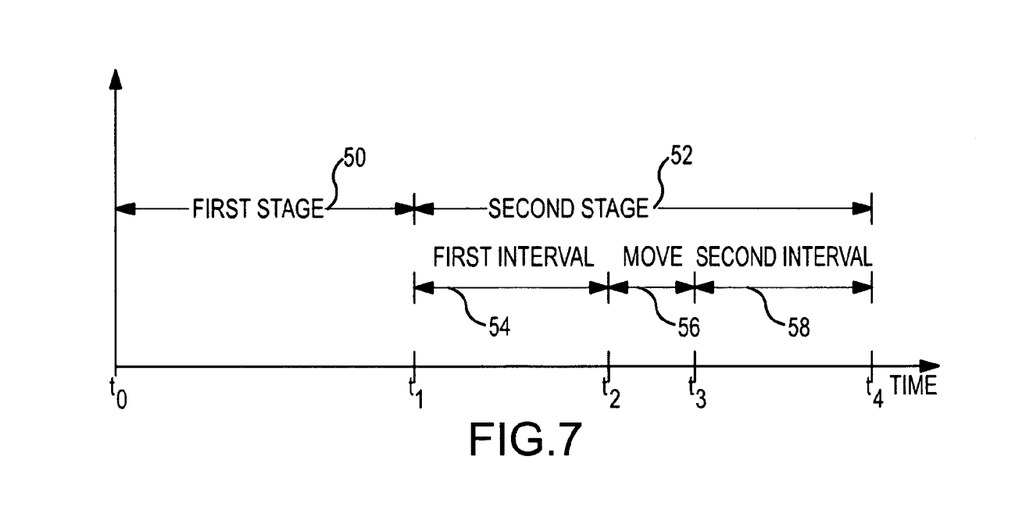
FIG. 7 is a timing diagram showing a variation of the embodiment of FIGS. 5-6 that involves moveable electrodes, where the second stage is sub-divided into first and second sub-stages.

FIG. 7 is a timing diagram showing further embodiments that use only four electrodes rather than three pairs (six electrodes) as used in the first embodiment while maintaining efficient ablation. In one further embodiment, during the first stage, designated as interval 50 on the timeline, the first pair of electrodes 32 (electrodes 1A/1B) are used in the manner described above. However, during the second stage of ablation, designated as interval 52, bipolar ablation may be conducted using only the second pair of electrodes 36 (i.e., electrodes 2A+ and 2B−). These electrodes may be positioned as in FIG. 3. A still further embodiment involves the concept of sub-dividing the second stage interval 52. During a first sub-stage, designated as first interval 54, the second pair of electrodes 36 (i.e., electrodes 2A+/2B−) are situated as shown in FIG. 3 and are then energized as described above to conduct bipolar ablation. Then, during interval 56, the second pair 36 (electrodes 2A+/2B−) are moved and are placed in the positions of electrodes 2A−/2B+ of FIG. 3, in essence in the same place as the now-omitted third pair of electrodes 38. The electrodes 2A+/2B− (now-moved) are then energized as described above to conduct bipolar ablation.

Figure 8:
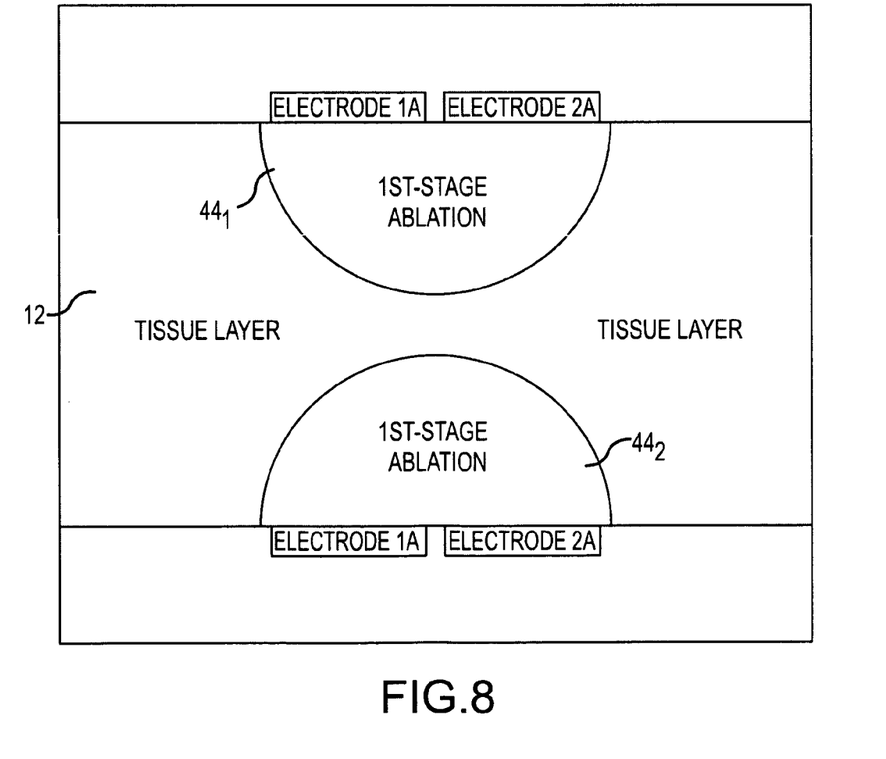
FIGS. 8-9 are cross-sectional views of a tissue site in a further embodiment involving moveable electrodes and an optional mechanical clamp.
Figure 9:
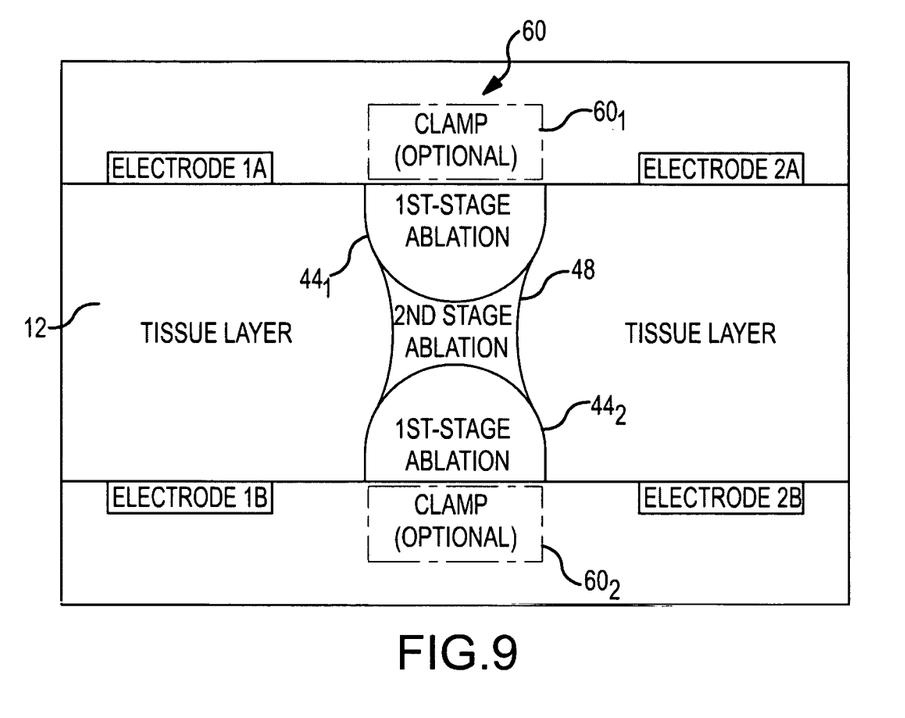

FIGS. 8-9 are cross-sectional views of the tissue site 12 showing a still further embodiment that involves four moveable electrodes. Before the first stage of ablation, electrodes 1A and 2A are electrically connected and are placed relatively close to each other and disposed approximately opposite the electrodes 1B and 2B, which are themselves electrically connected to each other. In effect, the two pairs of electrodes, taken together, are configured in the opposing arrangement described above in connection for the electrode pair 34 (1A/1B) in the embodiment of FIGS. 3 and 5-6.

As shown in FIG. 8, during the first stage, bipolar ablation is performed between the electrodes 1A/2A (i.e., both driven in a positive phase, such as per signal 40 in FIG. 4) and the electrodes 1B/2B (both driven in a negative phase, such as per signal 42 in FIG. 4). This first stage forms a pair of first stage ablation regions $44_1$, $44_2$ as shown.

FIG. 9 is a cross-sectional view showing the reconfiguration of the electrodes, as compared to FIG. 8, for purposes of conducting the second stage ablation. For the second stage, the two electrode pairs 1A/1B and 2A/2B are moved away from their first location (i.e., the opposing arrangement) to a second location where they are laterally spread apart, away from the first stage ablation regions $44_1$, $44_2$. Preferably, in the second location, the electrodes have at least a predetermined minimum lateral spacing between the inner edges of the electrodes and the outer edges of the first stage ablation regions $44_1$, $44_2$. This new spacing constitutes a dual diametrical arrangement, similar to that shown in FIG. 3 for the first embodiment. Next, the two pair of electrodes are electrically reconfigured/reconnected in pairs 1A-1B and 2A-2B with these pairs being driven in the opposite phases (e.g., electrode pair 1A-1B being driven in a positive phase, such as per signal 40 in FIG. 4, while electrode pair 2A-2B is driven in a negative phase, such as per signal 42, or switching positive/negative phase orientation would also work). Energizing these reconfigured pairs results in the formation of the second stage ablation region 48, as shown. One advantage of this embodiment is the reduced number of electrodes.

One challenge, however, is that this embodiment necessarily involves moving the electrodes and in addition, during the second stage, the tissue site 12 is no longer clamped across the center near the first ablation regions (i.e., where the two electrodes pairs were previously located during the first stage). To address this challenge, in a still further embodiment, an optional mechanical clamping device 60 comprising clamp members $60_1$ and $60_2$ may be used, separable or partially separable from the RF electrodes 1A/1B and 2A/2B. As shown, the mechanical clamping device 60 takes the place vacated by the two electrode pairs after the first stage, thereby ensuring consistent compression through the tissue site 12. This is particularly important where the tissue layer includes multiple, individual layers, such as may exist when conducting epicardial ablation (i.e., "pinching" or "folding" tissue, thereby lapping two individual layers).

In another embodiment, only two movable electrodes (and optionally a clamp) are used. For the first ablation stage, these electrodes are put in the central position (34 in FIG. 3). For the two substages of the second ablation stage, these electrodes are repositioned into positions 36 and 38 (FIG. 3) for one and the other substages, respectively. The optional clamp could be placed in the middle of the tissue site (FIG. 9), when the two electrodes are removed herefrom.

Figure 10:
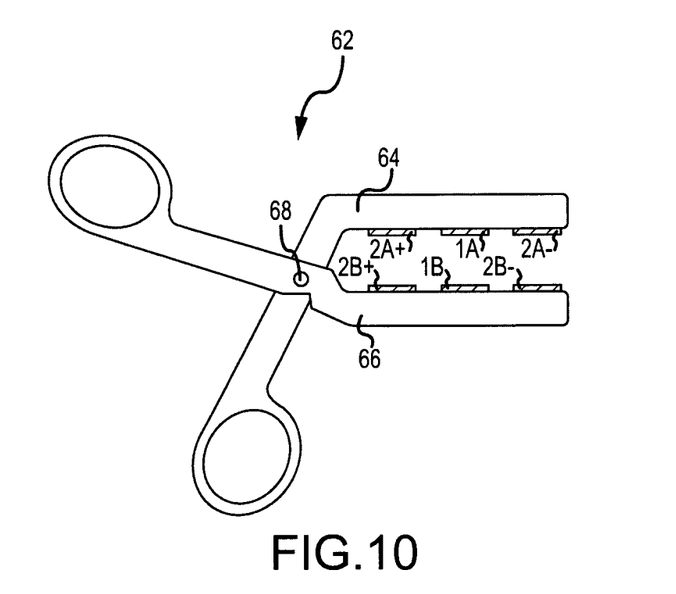
FIG. 10 is a side view of a first, scissors-type apparatus embodiment for performing the ablation method of FIG. 2.

FIG. 10 is a side view of an apparatus 62 configured for use in performing the ablation method described herein. The apparatus 62 may include a pair of opposing substantially resilient elongate members 64, 66 that couple the electrodes 1A/1B, 2A+/2A− and 2B+/2B− for RF energy delivery therebetween. The elongate members may comprise clamping members 64, 66 (as shown in FIG. 10) actuated via a pivot 68 in a scissors-like fashion.

Figure 11:
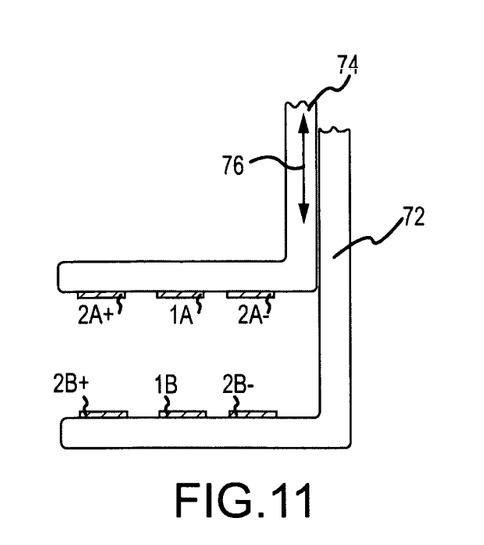
FIG. 11 is a side view of a second, slide-type apparatus embodiment for performing the ablation method of FIG. 2.

FIG. 11 is a side view of apparatus 70 also configured for use in performing the ablation method described herein. The apparatus 70 may also include a pair of opposing substantially resilient elongate members designated 72, 74 configured so as to be slideably coupled so that one member (e.g., member 72) is fixed and the other member (e.g., member 74) is moveable in direction 76 toward/away from the fixed member 72.

Figure 12:
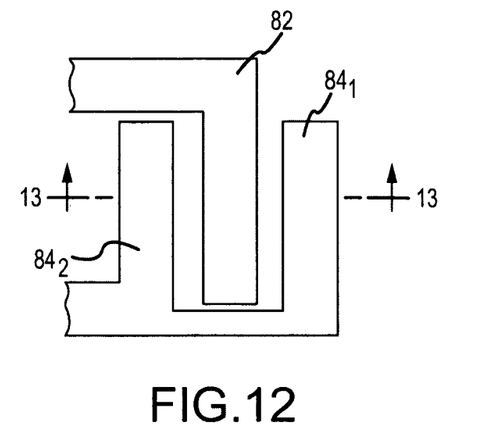
FIG. 12-13 are top and side views, respectively, of a third, three-arm scissors-type apparatus embodiment for performing the ablation method of FIG. 2.
Figure 13:
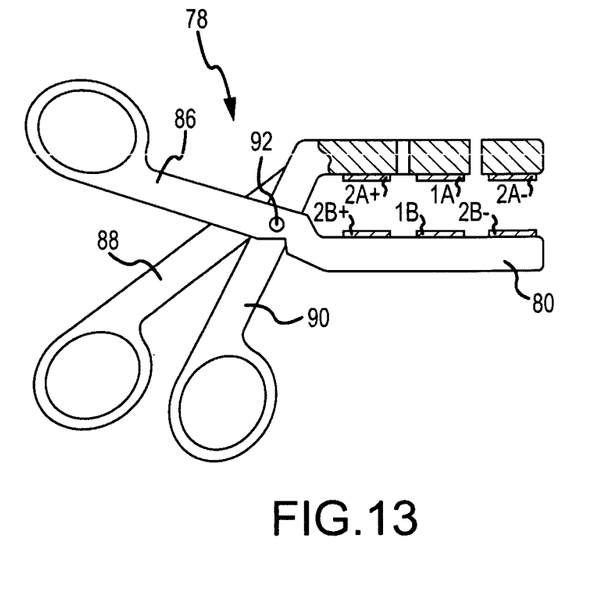

FIGS. 12-13 are partial top and side views, respectively, of a still further 3-arm, scissors-type embodiment, designated apparatus 78. The apparatus 78 includes a lower, clamping member 80, a first upper clamping member 82 and a second upper clamping member 84 comprised of a pair of individual members $84_1$ and $84_2$. Handle portions 86, 88 and 90 are used to control the motion of members 80, 82 and 84, respectively. The apparatus 78 includes a main pivot 92. The apparatus 78 provides the means to separately move each clamping arm 80, 82 and 84 independent of each other. Thus, clamping arms 80, 82 can be moved into position so that electrodes 1A/1B apply a clamping force to the tissue site 12 during a first stage, while the clamping arm 84 can remain positioned so that electrodes 2A+/2A− and 2B+/2B− do not contact the tissue site and thus do not exert a clamping force on the tissue. During the second stage, the clamping arm 84 can be moved into position so that electrodes 2A+/2A− and 2B+/2B− contact the tissue site and thus exert a clamping force to the tissue. In the embodiments of FIGS. 10-13, suitable elongate conductors, switches couple the electrodes to the RF generator 14. Thus, generally, the apparatus 78 is configured such that the elongate members comprise at least two pairs of opposing members so that both pairs can engage a target tissue site in a compressive state and at least one can be relaxed in a non-compressive state thereby not engaging the target tissue site. In one form the members of the embodiments described herein are designed and fabricated of biocompatible material and of dimension providing ease of pericardial access via, for example, a sub-xiophoid incision to access one or more pulmonary veins of a subject.

The ablation process may be effectively monitored by checking the impedance between one or more different pairs of electrodes. Taking the first embodiment (i.e., FIGS. 3 and 5-6) as exemplary, the first stage ablation may be terminated ("first stage termination conditions") when the impedance between electrode 1A and electrode 1B approximately saturates (i.e., when, after increasing initially after ablation starts, levels off to an approximately constant or level value). During the second stage, the impedance between a number of electrode pairs may be monitored, for example: (1) between electrodes 2A+ and 2B+ (i.e., to estimate if any unwanted RF ablation occurs near these electrodes, which would reveal itself by an increase in impedance value); (2) between electrodes 2A− and 2B− (i.e., also to estimate if any unwanted RF ablation occurs near these electrodes); (3) between electrodes 2A+ and 2B−, the diametrical arrangement, to estimate if the second stage ablation succeeded (e.g., forming a satisfactory second stage ablation region 48); and/or (4) between electrodes 2A− and 2B+, the diametrical arrangement, also to estimate if the second stage ablation succeeded (e.g., forming a satisfactory second stage ablation region 48). The latter two situations may be monitored, for example, to ascertain impedance saturation as described above, and used to determine when to terminate the second stage ("second stage termination conditions"). It should be understood, as alluded to above, that the impedance monitoring may be performed manually (i.e., as observed by the user), or, alternatively, may be implemented in automated monitoring/automatic start/stop of the ablation stages. In the automated embodiment, the main controller 18 of the ablation generator 14 may be configured in software to implement the above steps, consistent with the description herein.

It should be understood that the system 10, particularly the RF ablation generator 14, as described above may include conventional processing apparatus known in the art, capable of executing pre-programmed instructions stored in an associated memory, all performing in accordance with the functionality described herein. Certain aspects of the methods described herein may be programmed (as indicated), with the resulting software being stored in an associated memory and where so described, may also constitute the means for performing such methods. Implementation in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

In addition, the ablation electrodes described herein may be coupled to only an RF generator or one or more electrodes can also couple to a cardiac pacing circuit and/or a cardiac sensing circuit or impedance measuring circuit (as described above) according to various forms of the invention. The pacing and/or sensing circuitry can be used to confirm transmurality of a particular lesion set (e.g., a continuous transmural lesion around a plurality of pulmonary veins) whether or not the set was produced by a system according to the foregoing or in part by another apparatus. That is, pacing or sensing "above" the lesion set (above natural sinus rhythm) should not conduct or capture the myocardium thus indicating continuity of the lesion set. Likewise, sensing above the lesion set should not detect cardiac activity (or at least not at typical amplitude(s)).

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of ablating a tissue site having a depth, comprising the steps of:
   during a first stage, conducting bipolar ablation between a first pair of electrodes in an opposing arrangement on opposing sides of the tissue site so as to form a pair of opposing first stage ablation regions in the site extending from respective sides of the tissue site towards a center of said tissue site, said first stage being conducted in accordance with at least one of a selected power and time duration parameter such that upon termination of said first stage ablation, said pair of opposing first stage ablation regions together extend less than said depth of said tissue site; and during a second stage, conducting bipolar ablation between a second pair of electrodes in a diametrical arrangement with respect to the first stage ablation regions to form a second stage ablation region in the center of said tissue site different than said first stage ablation regions and that is intermediate said first stage ablation regions to complete the ablation through the entire depth of the tissue site.

2. The method of claim 1 wherein the diametrical arrangement is a first diametrical arrangement, and wherein said method further comprises the step of conducting bipolar ablation, during the second stage, between a third pair of electrodes in a second diametrical arrangement with respect to the first stage ablation regions.

3. The method of claim 2 wherein the second pair of electrodes is different from the third pair of electrodes.

4. The method of claim 1 wherein the second stage comprises first and second intervals, and wherein said step of conducting bipolar ablation during the second stage comprises the sub-steps of:

conducting bipolar ablation during the first interval using the second pair of electrodes in the diametrical arrangement;

moving the second pair of electrodes to a second diametrical arrangement;

conducting bipolar ablation during the second interval using the second pair of electrodes in the second diametrical arrangement.

5. The method of claim 1 further including the steps of configuring, for the first stage, the first and second pairs of electrodes so as to be disposed in the opposing arrangement, and re-configuring, for the second stage, the first and second pairs of electrodes so as to be in a dual diametrical arrangement that includes the diametrical arrangement.

6. The method of claim 5 wherein said step of re-configuring includes the sub-step of:

moving the first and second pairs of electrodes from a first location corresponding to the opposing arrangement to a second location corresponding to the dual diametrical arrangement.

7. The method of claim 6 further including the step of: mechanically clamping the tissue site proximate the first location.

8. The method of claim 1 wherein said step of conducting bipolar ablation during the second stage includes the sub-step of:

electrically isolating the first pair of electrodes from the tissue site.

9. The method of claim 8 wherein said electrically isolating step includes the sub-step of:

removing the first pair of electrodes from contact with the tissue site.

10. The method of claim 8 wherein said electrically isolating step includes the sub-step of:

interposing a high impedance between the first pair of electrodes and a source of ablation power.

11. The method of claim 10 wherein said interposing step includes the sub-step of selectively advancing and withdrawing an electrically insulative sheath over one or more of the electrodes.

12. The method of claim 1 wherein said steps of conducting bipolar ablation include the sub-step of:

powering in counter-phase the electrodes of at least one of the first and second pairs of electrodes.

13. The method of claim 12 wherein said powering step further includes the sub-steps of:

applying a first signal to one of the electrodes of one of the first and second electrode pairs;

applying a second signal to the other one of the electrodes of the one pair of electrodes wherein the first and second signals are offset in phase by 180 electrical degrees.

14. The method of claim 13 wherein the first and second signals are alternating current (AC) signals having a predetermined frequency.

15. The method of claim 14 wherein the predetermined frequency is in the radio frequency (RF) range between about 50 kHz and 500 kHz.

16. The method of claim 1 wherein said steps of conducting bipolar ablation include the sub-step of:

powering the first pair of electrodes at a substantially constant power.

17. The method of claim 1 further including the steps of: monitoring an impedance of the tissue site;

discontinuing bipolar ablation during the first stage when the monitored impedance satisfies predetermined criteria.

18. The method of claim 17 wherein said predetermined criteria includes a saturation condition.

19. The method of claim 1 further including the step of: selecting a first width for the electrodes of the first pair of electrodes for the first stage that is no greater than a second width associated with the second pair of electrodes for the second stage.

20. The method of claim 1 further including the step of: selecting a length-to-width aspect ratio of the electrodes of the first pair of electrodes that is at least greater than one.

21. The method of claim 20 wherein the aspect ratio is greater than about three (3).

22. The method of claim 1 further comprising:

after termination of said first stage, beginning said second stage.

* * * * *